(12) United States Patent
Kong et al.

(10) Patent No.: US 11,993,634 B2
(45) Date of Patent: May 28, 2024

(54) RECOMBINANT VARICELLA-ZOSTER VIRUS (VZV) VACCINE

(71) Applicant: BEIJING LUZHU BIOTECHNOLOGY CO., LTD., Beijing (CN)

(72) Inventors: Jian Kong, Beijing (CN); Pei Hong Jiang, Beijing (CN); Ling Peng, Beijing (CN); Shuai Yang, Beijing (CN); Leitao Xu, Beijing (CN); Kun Zhang, Beijing (CN)

(73) Assignee: BEIJING LUZHU BIOTECHNOLOGY CO., LTD., Beijing (CN)

( * ) Notice: Subject to any disclaimer, the term of this patent is extended or adjusted under 35 U.S.C. 154(b) by 245 days.

(21) Appl. No.: 17/422,835

(22) PCT Filed: May 14, 2020

(86) PCT No.: PCT/CN2020/090200
§ 371 (c)(1),
(2) Date: Jul. 14, 2021

(87) PCT Pub. No.: WO2021/103434
PCT Pub. Date: Jun. 3, 2021

(65) Prior Publication Data
US 2022/0363721 A1  Nov. 17, 2022

(30) Foreign Application Priority Data

Nov. 29, 2019 (CN) .......................... 201911203663.2

(51) Int. Cl.
| C07K 14/005 | (2006.01) |
| A61K 9/19 | (2006.01) |
| A61K 39/25 | (2006.01) |
| A61K 39/39 | (2006.01) |
| A61P 31/22 | (2018.01) |
| A61K 39/00 | (2006.01) |

(52) U.S. Cl.
CPC .............. *C07K 14/005* (2013.01); *A61K 9/19* (2013.01); *A61K 39/25* (2013.01); *A61K 39/39* (2013.01); *A61P 31/22* (2018.01); *A61K 2039/5254* (2013.01); *A61K 2039/545* (2013.01); *A61K 2039/55505* (2013.01); *A61K 2039/6056* (2013.01); *C07K 2319/30* (2013.01); *C12N 2710/16722* (2013.01); *C12N 2710/16734* (2013.01)

(58) Field of Classification Search
None
See application file for complete search history.

(56) References Cited

FOREIGN PATENT DOCUMENTS

| CN | 102517302 A | 6/2012 |
| CN | 108472309 A | 8/2018 |
| CN | 110343722 A | 10/2019 |

OTHER PUBLICATIONS

PCT International Search Report for International Application No. PCT/CN2020/090200, dated Aug. 31, 2020, 7 pages.
Huang et al., "Non-official translation: Research Progress on Fc-Fusion Proteins as Drugs," Heilongjiang Science and Technology Information, Jul. 25, 2016, p. 164.
Zell, R. "membrane glycoprotein E [Human alphaherpesvirus3]" GENBANK:AEW88548.1, Feb. 3, 2012, sequence.
Acta Universitatis Medicinalis Anhui, Mar. 2015, 50 (03), pp. 259-264.
"Cloning and expression of varicella zoster virus glycoprotein E extracellular domain and it's application," Anhui Medical University, master and doctoral theses, (c) 1994-2021 China Academic Journal Electronic Publishing House, May 2015.
Caminschi et al. "Boosting antibody responses by targeting antigens to dendritic cells," Trends in immunology, Feb. 2012, vol. 33, No. 2.
Li et al., "Eukaryotic expression and identification of extracellular domain of glycoprotein E of varicella-zoster virus," Chinese Journal of Biologicals, Nov. 2016, vol. 29, No. 11, pp. 1159-1161.
Dai et al,., "Differential signal transduction, membrane trafficking, and immune effector functions mediated by Fc [gamma]RI versus Fc[gamma]RIIa, " The American Society of Hematology, Blood, Jul. 9, 2009, vol. 114, No. 2, pp. 318-327.
Debrus et al., "Varicella-Zoster Virus Gene 63 Encodes an Immediate-Early Protein That is Abundantly Expressed during Latency," American Society for Microbiology, Journal of Virology, May 1995, vol. 69, No. 5, p. 3240-3245.
Arvin et al., "Equivalent recognition of a varicella-zoster virus immediate early protein (IE62) and glycoprotein I by cytotoxic T lymphocytes of either CD4+ or CD8+ phenotype," The Journal of Immunology, 1991, 146, 257-264.

(Continued)

*Primary Examiner* — Agnieszka Boesen
(74) *Attorney, Agent, or Firm* — Hoffman Warnick LLC

(57) ABSTRACT

The present disclosure discloses a recombinant varicella-zoster virus (VZV) vaccine, including a fusion protein formed by an amino acid sequence of an extracellular domain of a recombinant glycoprotein gE of a live attenuated VZV strain (OKA strain) gene and an Fc fragment of human immunoglobulin. The present disclosure further provides preparation and use of the fusion protein, a corresponding recombinant gene, a eukaryotic expression vector, etc. The fusion protein of the present disclosure has prominent immunogenicity and can induce the high-level expression of neutralizing antibodies in serum.

10 Claims, 7 Drawing Sheets

Specification includes a Sequence Listing.

(56) References Cited

OTHER PUBLICATIONS

Sharp et al., "Kinetics and Viral Protein Specificity of the Cytotoxic T Lymphocyte Response in Healthy Adults Immunized with Live Attenuated Varicella Vaccine," The Journal of Infectious Diseases, 1992, 165, 852-858.
Huang et al., "Specific Lysis of Targets Expressing Varicella-Zoster Virus gpl or gpIV by CD4+ Human T-Cell Clones," Journal of Virology, May 1992, vol. 66, No. 5, p. 2664-2669.
Li et al., "Construction of the eukaryotic expression vector containing varicella-zoster virus glycoprotein E," Practical Journal of Clinical Medicine 3(3):25-26 (2006).
Sabella et al., "Immunization with the Immediate-Early Tegument Protein (Open Reading Frame 62) of Varicella-Zoster Virus Protects Guinea Pigs against Virus Challenge," Journal of Virology, Dec. 1993, vol. 67. No. 12, p. 7673-7676.
Arvin et al., "Memory Cytotoxic T Cell Responses to Viral Tegument and Regulatory Proteins Encoded by Open Reading Frames 4, 10, 29, and 62 of Varicella-Zoster Virus," Viral Immunology, vol. 15, No. 3, 2002, p. 507-516.
Haumont et al., "Purification, characterization and immunogenicity of recombinant varicella-zoster virus glycoprotein gE secreted by Chinese hamster ovary cells," Virus Research 40, 1996, 199-204.

RECOMBINANT VARICELLA-ZOSTER VIRUS (VZV) VACCINE

TECHNICAL FIELD

The present disclosure relates to a vaccine preparation, and specially designs a vaccine preparation that can induce human immune system to produce neutralizing antibodies against a recombinant varicella-zoster virus (VZV) glycoprotein E (gE) fusion protein.

BACKGROUND ART

VZV, a member in the subfamily Alphaherpesvirinae of the family Herpesviridae, is a double-stranded DNA virus with a diameter of 150 nm to 200 nm. Morphologically, VZV has a concentric structure composed of nucleic acid core, protein capsid, and envelope. The VZV genome is a linear double-stranded DNA molecule of about 125 kb, which includes a unique long sequence (UL) of about 100 kb and unique short sequences (US) of about 5.4 kb that are separated from each other by terminal and internal repeats of 6.8 kb, with 72 open reading frames (ORFs) in total. In addition to protein molecules associated with the replication, transcription, packaging, release, and other biological activities of VZV and proteins interacting with host cells, the VZV genome encodes 8 glycoproteins of glycoprotein B (gB), glycoprotein C (gC), gE, glycoprotein H (gH), glycoprotein I (gI), glycoprotein K (gK), glycoprotein L (gL), and glycoprotein M (gM), which play an extremely important role in the maturation and packaging of VZV. The gE includes 623 amino acids (AA) and is encoded by an ORF68 gene, which consists of 1,872 bases and is located in a short sequence region of the VZV genome. The gE has a hydrophilic extracellular domain of 544 AA (including signal peptide) at the N-terminus, and has a hydrophobic transmembrane domain of 17 AA and an intracellular domain of 62 AA at the C-terminus. As a type I membrane protein, the gE is an essential glycoprotein for the production of infectious VZV particles and is also a glycoprotein with the strongest antigenicity and the highest content on the viral envelope and the infected cell membrane. Moreover, the gE is also widely present on a surface of VZV particles and a cell membrane of host cells and in cytoplasm of host cells and can induce cellular immunity and humoral immunity.

The gE of VZV includes two epitope coding regions el and cl. The epitopes are stable among VZV strains from different regions, have high conservation, and are suitable candidate vaccine antigen subunits. The gE is present on a surface of VZV particles and infected cells and in cytoplasm of infected cells, which exists in different glycopeptide forms at different maturity stages of VZV. A gE molecule includes a transport signal and can participate in the assembly of viral proteins and the envelope formation in Golgi apparatus. In the serum of patients with varicella and herpes zoster at the convalescent stage, anti-VZV antibodies mainly target the three glycoproteins of gB, gH, and gE, especially target the gE. The specific humoral and cellular immunity produced by a body under the induction of gE can protect the body from virus attack. The gE includes phosphorylated high-mannose O-chain and N-chain complex glycans, which can cooperate with gI to bind to the Fc segment of human IgG. gE and gI are covalently linked to serve as an Fc receptor on a surface of infected cells.

VZV enters local lymph nodes through the respiratory mucosa epithelium and replicates during primary infection, lymphocytes infected with VZV then enter the blood circulation through the lymphatic circulation and the peripheral blood mononuclear cells (PBMCs) are infected, and the virus spreads to the skin with the bloodstream, which is clinically manifested as varicella. After varicella is cured, the virus stays latent in craniocerebral ganglia, spinal dorsal root ganglia, autonomic neurons, or enteric neurons. When the resistance of a body is reduced, the latent virus is reactivated, replicates, and migrates to the skin along peripheral nerves, which is clinically manifested as herpes zoster.

VZV is highly infectious. Patients with varicella or herpes zoster are the only source of infection. VZV is mainly transmitted through air droplets and direct contact. Patients with varicella excrete the virus through saliva or eye fluid 2 days before the appearance of rash. The blister fluid of patients with varicella or herpes zoster includes infectious virus particles. Susceptible people will be infected if inhaling droplets produced by the patients with varicella or herpes zoster during breathing, and will also be infected if directly contacting with the blister fluid from skin lesions, where the more the skin lesions, the stronger the infectivity. Varicella may occur in infected susceptible people, but the infection does not directly cause herpes zoster.

Seroepidemiological surveys show that 95% to 97% of women at a child-bearing age are positive for serum anti-VZV antibodies, so there is a very low chance for an infant to suffer from VZV infection within 6 months after birth. Serum anti-VZV antibody-negative adults, infants born by serum anti-VZV antibody-negative pregnant women, immunocompromised people, fetuses of pregnant women who have had varicella in the 4th to 5th months of pregnancy, and newborns born by mothers who have had varicella before and after delivery are all prone to severe primary infection of VZV. The elderly, immunocompromised people, children whose mothers have had varicella during pregnancy, and children who have had varicella one year after birth have an increased risk of developing herpes zoster.

More than 95% of young people in North America and Europe are positive for serum anti-VZV antibodies, so they are at risk of developing herpes zoster. According to statistics based on the population base, the herpes zoster has an incidence of 3 to 5 per 1,000 persons each year, including: 3 to 10 per 1,000 persons each year in the Asian-Pacific region, 10. 4 per 1,000 persons each year in South Korea, 10. 9 per 1,000 persons each year in Japan, 3.4 to 5.8 per 1,000 persons each year in mainland of China, and 4.89 to 5.67 per 1,000 persons each year in Taiwan of China. There is currently a lack of data on the incidence of herpes zoster in Africa.

About 13% to 47% of patients with herpes zoster have complications or sequelae, which mainly involve the nervous system and eyes. Nervous system complications include post-herpetic neuralgia (PHN), Ramsay-Hunt syndrome, Bell's palsy, meningitis, myelitis, and transient ischemic attack (TIA) or stroke. Ocular complications mainly include herpes zoster ophthalmicus (HZO).

PHN is the most common sequela of herpes zoster, which has an internationally accepted definition that the pain continuously lasts for more than 90 days after the appearance of rash. About 30% to 50% of PHN lasts for more than 1 year, and a few can last as long as 10 years. About 5% to 30% of patients with herpes zoster have PHN, 10% to 20% is reported in most literatures, and there is 8.6% to 13.8% in mainland of China. The incidence of PHN increases with the age of patients, there is a PUN incidence of about 8% among patients ≥50 years old, and there is a PHN incidence as high as 33% among patients ≥80 years old. Relatively clear PHN-susceptible factors include advanced age, severe prodromal symptoms, severe rash, heavy pain, and weak immunity. People with trigeminal nerve involvement, accompanied SLE, diabetes, or neuropsychiatric disorders are also susceptible to PHN.

HZO is caused by the involvement of the ophthalmic division of the trigeminal nerve after the latent VZV is reactivated and replicated. According to statistics based on the population base, HZO has an incidence of 30.9 per 100,000, which reaches 104.6 per 100,000 among people aged≥65. According to statistics based on the base number of patients with herpes zoster, HZO has an incidence of 10% to 20%, which also increases with age. The clinical manifestations of HZO include blepharitis, keratitis, conjunctivitis, scleritis, uveitis, or acute progressive retinal necrosis. About 2.5% of HZO patients in the United States undergo eye damage, 6% of which are blind. About half of HZO patients undergo skin damage, about 21% of which is eventually developed into PHN.

Elderly patients or immunocompromised patients can also undergo repeated attack of herpes zoster, spread of skin lesions, accompanied bacterial infections, or verrucous hyperplasia, which can also lead to virus resistance. In severe cases, multiple organs such as lungs, gastrointestinal tract, and brain may even be involved, and hepatitis, pancreatitis, pneumonia, myocarditis, esophagitis, or peptic ulcer may occur before the appearance of herpes zoster rash, which easily results in misdiagnosis.

People who have been inoculated with an attenuated VZV strain (OKA strain) or naturally infected with VZV can obtain protective immunity. The live attenuated vaccine of the OKA strain has been approved by the U.S. FDA, the National Medical Products Administration of China, the European Union, and other institutions for child vaccination to prevent children from being infected by wild-type VZV. The high-dosage live attenuated vaccine of the OKA strain has been approved by the U.S. FDA and the European Union for vaccination in elderly people over 50 years old to prevent them from suffering from diseases caused by VZV such as intercostal neuralgia or reduce their risk of developing such diseases. At present, more than 60 countries and regions including the European Union and the United States have recommended Zostavax for people with normal immune function ≥50 years old to prevent herpes zoster and PHN. The Zostavax vaccine is inoculated by injecting a single dose (0.65 mL, including 19,400 PFU of virus) subcutaneously into a deltoid region of an upper arm. Occasionally, adverse reactions such as headaches and injection local reactions may occur. It has be verified by large-scale multicenter clinical trials that, after vaccination, the herpes zoster incidence is reduced by 69.8% in people with normal immune function at 50 to 59 years old, and the herpes zoster incidence, PHN incidence, and disease burden are reduced by 51.3%, 66.5%, and 61.1% respectively in people ≥60 years old. The preventive efficiency of Zostavax gradually decreases with the age of vaccination objects. People with severe immunosuppression and pregnant women are prohibited from vaccination. Therefore, it is particularly urgent to prepare safer and more effective vaccines than existing vaccines. The GSK company develops a herpes zoster subunit vaccine prepared from recombinant VZV gE and AS01B adjuvant. When the subunit vaccine is inoculated into people with normal immune function ≥50 years old, the herpes zoster incidence and the PHN incidence are reduced by 97.2% and 91.2%, respectively; and when the subunit vaccine is inoculated into people ≥70 years old, the herpes zoster incidence and the PHN incidence are reduced by 89.8% and 88.8%, respectively. The subunit vaccine shows a better effect than the live attenuated vaccine Zostavax, and may have promising application prospects. The AS01B diluent used in the recombinant VZV gE vaccine includes oily adjuvants such as QS21, 3D-MPL, and phosphatidylcholine (PC). Therefore, although the effect of the recombinant VZV gE vaccine is significantly better than that of the VZV live attenuated vaccine Zostavax, the recombinant VZV gE vaccine will cause the formation of nodules at an injection site that require a short time or a long time to disappear.

CN102517302A discloses a method for recombinantly expressing VZV truncated gE and use thereof. In this method, a VZV truncated gE (where a transmembrane domain and an intracellular domain are removed and a His tag is added) gene is introduced into host cells for expression to obtain the recombinant VZV truncated gE. The expression method helps to increase an expression level of a target protein, simplifies the downstream purification work, and can easily realize the large-scale production of a protein. The recombinant protein can be used as a capture antigen for the indirect ELISA assay of VZV specific immunoglobulins in plasma samples, which can improve the accuracy of clinical diagnosis of VZV infection. Moreover, the recombinant protein can also be used in other fields that require VZV specific immunoglobulins for high-throughput detection. A product of this method is a prokaryotically-expressed non-glycosylated protein, which is mainly used for the detection of previous VZV infections, and is not suitable for preparing immune compositions or human vaccines that require complex glycosylation to generate serum neutralizing antibodies for VZV. Li Fumin et al. disclose amplification of a VZV gE gene by PCR, cloning of the gene into a eukaryotic expression vector pcDNA3.1, and identification of the gene by double enzyme digestion and sequencing. Results show that an amplified target gene includes the full-length gE gene, with a length of about 1.9 kb, and a gE gene-carrying recombinant expression vector is successfully constructed (Practical Journal of Clinical Medicine, 2006 (02)). Yi Xingxu et al. disclose a method for constructing a eukaryotic expression plasmid pCDNA3.1-gE with a VZV gE extracellular domain gene. After sequencing, the plasmid is transfected into COS-7 cells by lipofection, and cell lines stably expressing VZV gE are screened out by G418. The mRNA of VZV gE is detected by RT-PCR, and the immunoreactivity of gE is detected by western blot and indirect immunofluorescence (IIF). An expression product is purified by $Ni^{++}$-NTA column, and coated on ELISA plate to detect a VZV-IgG antibody level in 127 serum samples from normal children at 0 to 10 years old. Results show that a COS-7 cell line capable of stably expressing the VZV gE extracellular domain gene is successfully screened out; the mRNA of gE is detected by RT-PCR; as detected by western blot and IIF, the expressed gE is immunoreactive; and there is gE expression in both the COS-7 cell line and a culture supernatant thereof, with an expression level of about 0.632 µg/mL and a purity of about 90%. In the ELISA test, 127 serum samples from children at 0 to 10 years old are tested for VZV-IgG antibodies, with a total positive rate of 81.89%, and a specificity and sensitivity respectively of 93.75% and 88.24% (Acta Universitatis Medicinalis Anhui, 2015 (03)). These studies on VZV gE are mainly focused on realizing the expression of the protein in eukaryotic cells. The expression product has very low purity, which can only meet the actual needs of detection, and is far from reaching the quality requirements of human vaccines. There is no research on follow-up purification of the expression product, and there is also no report on use of the expression product in human vaccines.

Li Chunming et al. disclose a method for constructing a recombinant eukaryotic expression plasmid pCI-neo-gE537-His, and the method includes: infecting human diploid cells (2BS line) with VZV-Oka; extracting genomic DNA (gDNA); with the gDNA as a template, amplifying a gE537 target fragment by PCR; and cloning the target fragment into a vector pCI-neo to obtain the recombinant eukaryotic expression plasmid pCI-neo-gE537-His. After massive amplification, the plasmid is extracted and transfected into 293FT cells for transient expression, and an expression product is purified by a nickel column to obtain a target protein gE537-His. The purified product can specifically bind to the mouse anti-gE monoclonal antibody (mAb) at a relative molecular mass of about 90 KDa, and can react with anti-gE mAbs of mAb-10 and mAb-12 (Chinese Journal of Biologicals, 2016 (11)). Yi Xingxu discloses a method for the cloning and expression of a gene fragment for a VZV gE extracellular domain. The method is specifically as follows: The skin vesicle fluid clinically collected from patients with herpes zoster is inoculated to monolayer human embryonic fibroblasts for virus isolation; and isolated virus strains are subjected to characteristic cytopathic effect (CPE), IIF, and DNA sequencing analysis. Verified VZV strains clinically isolated are cultivated in vitro, and the gene fragment for a VZV gE extracellular domain is amplified by PCR to construct a prokaryotic expression plasmid gE-pET-32a (+) and a eukaryotic expression plasmid gE-pCDNA3.1/myc-His (−). After sequencing, the prokaryotic plasmid is transformed into competent Escherichia coli (E. coli) BL21 (DE3), and isopropyl-β-D-thiogalactopyranoside (IPTG) is used for induction to obtain a prokaryotically-expressed fusion protein of VZV gE. The specificity of the recombinant protein is identified by SDS-PAGE electrophoresis and western blot, and the expressed protein is subjected to purification and on-column refolding with $Ni^{++}$-NTA column. The eukaryotic plasmid is transfected into COS-7 cells by lipofection, the cell line stably expressing VZV gE is screened out by G418, and an expression product is purified by $Ni^{++}$-NTA column. The mRNA of the VZV gE gene is detected by RT-PCR, and the immunoreactivity of the gE fusion protein is assayed by western blot and IIF. Purified prokaryoticaly-expressed gE and eukaryotically-expressed gE are used to immunize New Zealand rabbits separately to obtain rabbit anti-VZV gE polyclonal antibodies (pAbs) (Anhui Medical University, master and doctoral theses). The above results show that the expression of VZV gE in animal cells is achieved, but obtained expression products have low purity.

Fc receptors are expressed on the surface of many innate immune cells, so Fc fragments are also widely used in the study of dendritic cell (DC) targeting. According to different antibody subtypes that the Fc receptors bind to, Fc receptors are divided into FcαR (IgA), Fcα/γR (IgA and IgM), FcεR (IgE), and FcγR (IgG). In addition, Fc receptors can also be divided into high-affinity receptors and low-affinity receptors according to affinity. High-affinity receptors bind to mAbs, and low-affinity receptors bind pAbs. In the study of DC targeting, the FcγR targeting was applied the earliest. Many published studies have shown that FcγR targeting can significantly increase the efficiency of antigen presentation in vitro and promote the binding of antigen to MEW II. Antigen targeting FcγR is finally presented to $CD4^+$ T cells to activate the TH1 signaling pathway (Dai X, Jayapal M, Tay H K, Reghunathan R, et al., Differential signal transduction, membrane trafficking, and immune effector functions mediated by FcγRI versus FcγRIIa. Blood. 2009; 114: 318-27).

The fusion protein constructed by the fusion expression of VZV gE (or an antigen derived from other pathogenic microorganisms) and an Fc fragment of an anti-DC receptor mAb is internalized by DCs. During an endocytosis process, the Fc recombinant protein or Fc coupling protein is degraded by intracellular proteinases, and formed antigenic peptides can be loaded onto MHC-1 and/or MHC-II molecules. The outstanding advantage of this Fc-mediated method is that antigens can be delivered directly to antigen presenting cells (APCs), which improves the efficiency of antigen presentation. Moreover, by this method, specific signaling pathways can also be selectively activated by targeting specific receptors on the surface of DCs (Caminschi I, Shortman K. Boosting antibody responses by targeting antigens to dendritic cells. Trends in immunology. 2012; 33: 71-7).

In the present disclosure, a gene encoding an extracellular domain of a VZV gE peptide chain is linked to a gene encoding the CH2-CH3 region of human immunoglobulin, an obtained target gene is inserted into a eukaryotic expression vector, and an obtained eukaryotic expression vector is transfected into Chinese hamster ovary (CHO) cells, where the VZV gE-Fc fusion protein is successfully expressed. The recombinant protein is purified by affinity chromatography, ion exchange chromatography, and molecular sieve chromatography, and possible viral contaminants are removed by virus inactivation, such that a highly-purified fusion protein is obtained. An Fc fragment of the fusion protein can bind to an Fc receptor on the surface of DCs in an immune system of a human body, thereby enhancing the antigen presentation efficiency of DCs, and high titer serum neutralizing antibodies can be produced after immunization.

SUMMARY

The present disclosure relates to a method for preventing and/or reducing a severity of herpes zoster and/or PHN, which includes administering an individual with an immunogenic composition that includes live attenuated VZV (OKA strain) or fully-inactivated VZV and a VZV antigen or a recombinant immunogenic derivative gE thereof.

The present disclosure also relates to a method for preventing or ameliorating VZV reactivation and/or PHN, and the method includes administering an individual in need with an immunogenic composition or a vaccine that includes a gE fusion protein or an immunogenic derivative or fragment thereof and an adjuvant.

In view of the above-mentioned problems in the prior art, one of the objectives of the present disclosure is to provide a gene for a VZV gE-Fc fusion protein to obtain a high-purity expression product of the VZV gE gene in mammals.

In order to achieve the above objective of the present disclosure, the present disclosure adopts the following technical solutions:

The present disclosure provides a recombinant VZV vaccine preparation, including a fusion protein formed by an amino acid sequence of an extracellular domain of a recombinant glycoprotein gE of a live attenuated VZV strain (OKA strain) gene and an Fc fragment of human immunoglobulin, where the fusion protein has an amino acid sequence shown in SEQ ID No. 1.

The vaccine preparation of the present disclosure may further include a vaccine adjuvant. The vaccine adjuvant may be an aluminum hydroxide adjuvant, an aluminum phosphate adjuvant, or a mixture of aluminum hydroxide and aluminum phosphate adjuvants.

Each dosage unit of the vaccine preparation of the present disclosure may include 5 μg to 200 μg of the fusion protein.

Preferably, each dosage unit of the vaccine preparation of the present disclosure may include 10 μg to 100 μg of the fusion protein.

More preferably, each dosage unit of the vaccine preparation of the present disclosure may include 20 μg to 60 μg of the fusion protein.

The vaccine preparation of the present disclosure may further include other substances that can enhance immunogenicity, and the other substances that can enhance immunogenicity include, but are not limited to: PC, lecithin, 3D-1MPL, long-chain fatty acid (ester), mineral oil, vegetable oil, sodium methylcellulose (MC-Na), sodium carboxymethylcellulose (CMC-Na), and cholesterol-containing liposome.

The vaccine preparation of the present disclosure may be a lyophilized preparation. The lyophilized preparation may be dissolved by an aluminum hydroxide adjuvant suspension before use, and then a resulting mixture may be thoroughly mixed and injected intramuscularly or subcutaneously.

The present disclosure further provides a recombinant gene capable of expressing the fusion protein of the present disclosure, and the recombinant gene has a DNA sequence shown in SEQ ID No. 2.

An expression vector for the fusion protein (hereinafter referred to as gE-Fc or VZV gE) of the present disclosure is formed by inserting a gE-Fc fusion gene into a mammalian cell expression vector.

The fusion protein of the present disclosure is an exogenous antigen or a derivative thereof that can efficiently trigger an immune system of a human body to produce an immune response, and the immune response refers to an induced response of an immune system of a body to produce high-titer serum neutralizing antibodies. Such a response can reduce the incidence of human herpes zoster diseases, or can alleviate pain such as intercostal neuralgia or symptoms caused by herpes zoster. A common technique in the art such as serum neutralizing antibody level or VZV gE (glycosylated protein) ELISA antibody level determination is used to assess the improvement of immune response, or known clinical criteria are used to assess the improvement in clinical symptom or sign levels.

As a preferred implementation, the above-mentioned expression product can be mixed with an aluminum adjuvant or another drug that enhances immunogenicity to obtain a preparation, which can be used in elderly people over 50 years old to prevent infectious diseases caused by herpes zoster such as intercostal neuralgia and can also be used in infants to prevent infections caused by VZV.

Like the protective antigens of various viruses, the protective antigens of VZV are also glycoproteins, especially gE which is the main glycosylated protein of VZV. Diversified glycosylation forms provide main neutralizing antigens for VZV. Existing studies have confirmed that serum antibodies against gE can neutralize VZV.

Other suitable antigens also include various glycoproteins, such as gB, gH, gC, gI, and IE63 (for example, see Huang et al., J. Virol. 1992, 66: 2664; Sharp et al., J. Inf. Dis. 1992, 165: 852; Debrus, J Virol. 1995 May, 69 (5): 3240-5; and references therein), IE62 (for example, see Arvin et al., J. Immunol. 1991 146: 257; Sabella J Virol. 1993 December, 67 (12): 7673-6; and references therein), ORF4 or ORF 10 (Arvin et al., Viral Immunol. 2002 15: 507), but the abundance of these glycoproteins on the VZV membrane is lower than that of gE, so these glycoproteins do not constitute the main source for a body to produce VZV neutralizing antibodies.

The present disclosure realizes the high-efficiency expression of a VZV gE gene in a mammalian expression system. Without changing an amino acid sequence, a VZV gE extracellular region gene is synthesized based on codon optimization according to a preferred codon of CHO cells, a gE-Fc fusion gene is constructed, and on this basis, a eukaryotic expression vector is constructed and transfected into CHO K1 cells. The Protein A affinity chromatography (HPLC) is used to detect the protein expression, and the ELISA is used to detect the binding activity of VZV gE to human anti-VZV specific immunoglobulin. It is confirmed that the secretion and expression of the VZV gE gene in CHO cells is successfully achieved. A serum neutralization test where rabbits and BALB/C mice are immunized with highly-purified VZV gE and obtained immune serum is used to neutralize OKA strain is conducted, and test results prove that the expressed VZV gE-Fc protein has prominent immunogenicity and high titer serum neutralizing antibodies can be produced after 2 immunizations.

The VZV gE antigen should be used at a dosage that can induce a body to produce a protective immune response without obvious adverse side effects. The dosage of the antigen varies with an adjuvant used and a way the adjuvant exists. Generally speaking, it can be expected that each dosage may include about 2 μg to 1,000 μg of VZV gE. When the VZV gE is used in humans, an aluminum adjuvant can be used for adsorption to reduce the number of injections, and when an aluminum adjuvant is used for adsorption, the use of 5~μg to 200 μg of VZV gE is expected to produce high titer neutralizing antibodies. A preferable dosage may include 10~μg to 100 μg of VZV gE, and an appropriate immunization dosage may include about 10 μg, 25 μg, 50 μg, 100 μg, or about 200 μg of VZV gE. The optimal dosage for adults may include 50 μg or 100 μg of VZV gE, and the optimal dosage for infants may include 10 μg or 20 μg of VZV gE.

The administration route of the vaccine preparation of the present disclosure may include, for example, topical administration, intranasal administration, mucosal administration, intradermal administration, intraperitoneal administration, subcutaneous injection, and intramuscular injection.

The vaccine preparation of the present disclosure may optionally be combined with adjuvants and/or (other) suitable carriers.

In the case of using a booster immunization regimen or in the case of using a multi-immunization regimen, 2, 3, 4, or more immunizations may be adopted. Regimens suitable for activation and booster may include immunization at an interval of 1, 2, 3, or 6 months.

A sequence of an extracellular domain of VZV gE envelope is a part of the sequence listed in Annex 1 of the present disclosure. The complete sequence of VZV gE was first published in Virus Research (Virus Research, Haumont et al. Vol. 40, 1996 p: 199-204).

Unless otherwise specified clearly in the context, the VZV gE or gE mentioned hereinafter includes truncated VZV gE or other fragments or derivatives of VZV gE-Fc.

The gE or derivatives or fragments thereof are liquid or lyophilized. Moreover, the gE or derivatives (gE-Fc), fragments, or polymers thereof may be present in a suspension with an aluminum adjuvant, or may be present in a solution or suspension with other immune enhancer components (for example, a solution or suspension with QS21, cholesterol, mineral oil, vegetable oil, fish oil, long-chain fatty acid, long-chain fatty acid ester, 3D-MPL adjuvant, etc.).

The gE or derivatives thereof can be encapsulated in polylactic acid (PLA) microcarriers, or in microcarriers formed from diglycolide/lactide copolymer. After the formed microcarriers are injected intramuscularly or subcutaneously, the encapsulated recombinant protein drug is slowly released within a specified time period to stimulate an immune system of a body to produce antibodies.

Compared with the prior art, the present disclosure has the following advantages:

1. The present disclosure uses mammalian cells (CHO) to efficiently express the secreted gE-Fc fusion protein, and an obtained target product is glycosylated protein, which is in the form mainly of dimer and secondly of monomer. Each dimer molecule includes 4 gE molecules. The fusion protein produced in the present disclosure has large molecular weight and strong immunogenicity.

2. The gE-Fc of the present disclosure is a fusion protein of an extracellular domain of VZV gE and an Fc fragment of human immunoglobulin (CH2-CH3 region). A commercial Protein A affinity chromatography packing can be used to achieve the high efficiency preliminary isolation and purification of the target protein, which minimizes the emission of environmental pollutants, and is environmentally friendly and conducive to the further purification of the target protein by ion exchange chromatography, molecular size exclusion chromatography, etc. in subsequent steps.

3. The recombinant gE-Fc fusion protein expressed by the CHO cells of the present disclosure is a glycosylated protein, which retains the spatial structure of the natural gE protein, exhibits prominent immunogenicity, and is promising and advantageous in large-scale popularization.

4. The Fc in the gE-Fc fusion protein provided by the present disclosure can bind to the Fc receptors on the surface of APCs existing in a human immune system to actively present gE antigens. Results of animal immunogenicity experiments show that, when the gE-Fc protein produced by the recombinant CHO cells of the present disclosure is used as an antigen to immunize rabbits and mice without oily adjuvants and immune stimulants, high titer serum neutralizing antibodies can still be produced.

DETAILED DESCRIPTION

The present disclosure is further illustrated through the following examples, but the examples are not intended to limit the present disclosure.

Example 1. Construction of Plasmid Expression Vector

1. Source of Gene Sequence

The VZV gE of the present disclosure was an extracellular domain (ECD, 31-546 aa) of the gE, with a total of 516 amino acids. The Fc fragment was human IgG1 Fc, with a total of 232 amino acids (Appendix: Amino Acid Sequence 1). A gene of the VZV gE and a gene of the Fc of human IgG1 were linked in tandem (Appendix: DNA sequence 2). The Nanjing Genscript Biotechnology Co., Ltd was entrusted to synthesize the gene sequence of the VZV gE-Fc fusion protein and insert the gene sequence into a pUC57-1.8K vector, and a synthesized gene included enzyme digestion site, Kozak sequence, signal peptide, target gene (2,244 bp), and stop codon, with a total length of 2,355 bp. Codon optimization was conducted when the recombinant gene was synthesized to facilitate the expression in CHO cells Cricetulus griseus.

2. Construction of Expression Plasmids Carrying the VZV gE-Fc Gene

A glycerol-preserved strain with the recombinant gene provided by the Nanjing Genscript Biotechnology Co., Ltd was inoculated into an LB (Amp$^+$) medium and cultivated at 37° C. and 180 rpm for 15 h, and the TaKaRa MiniBEST Plasmid Purification Kit Ver. 4.0 was used to extract the plasmid pUC57-gE-Fc; the plasmid pUC57-gE-Fc was digested with HindIII and EcoR enzymes to obtain a target gene fragment gE-Fc-H/E (with a size of about 2,300 bp); and the mammalian expression plasmid pXC-K383L was digested to obtain a vector fragment pXC-H/E (with a size of about 7,000 bp). The agarose gel electrophoresis result of the enzyme digestion products was shown in FIG. 1.

Figure 1:
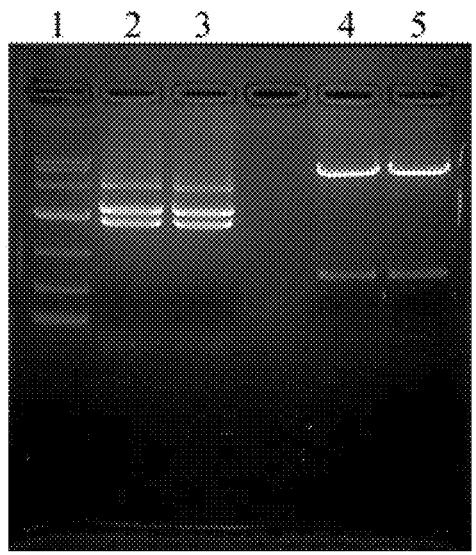
FIG. 1 shows an agarose gel electrophoresis result of enzyme digestion products of the VZV gE-Fc plasmids,
where lane 1: DL10000 DNA Marker (10,000 bp, 7,000 bp, 4,000 bp, 2,000 bp, 1,000 bp, 500 bp, and 250 bp),
lanes 2 and 3: enzyme digestion products of the plasmid pUC57-gE-Fc, and
lanes 4 to 5: enzyme digestion products of the plasmid pXC-K383L.
Figure 2:
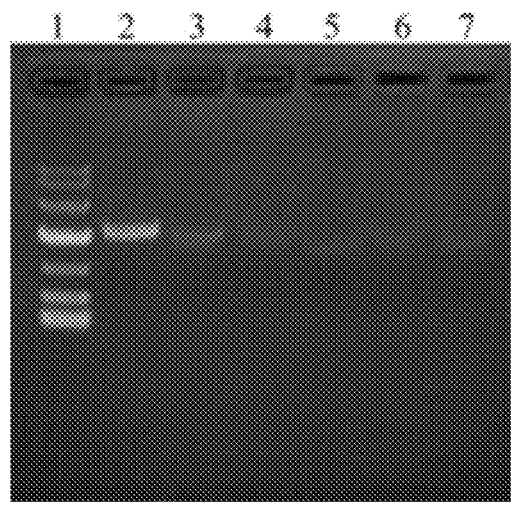
FIG. 2 shows positive clones obtained by colony PCR screening of the VZV gE-Fc recombinant plasmids,
where lane 1: DL10000 DNA Marker (10,000 bp, 7,000 bp, 4,000 bp, 2,000 bp, 1,000 bp, 500 bp, and 250 bp),
lanes 2 to 7: 6 clones gE-Fc-1 to 6 obtained by colony PCR screening.
Figure 3:
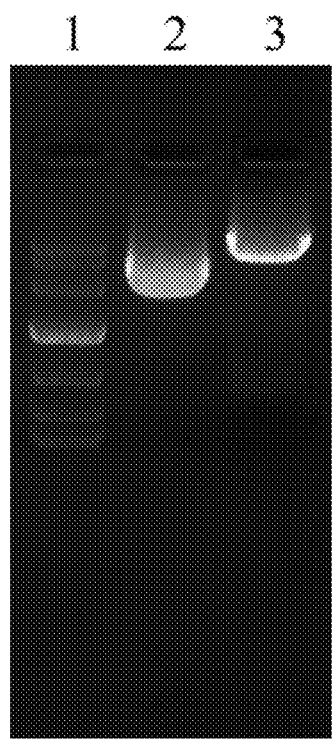
FIG. 3 shows an agarose gel electrophoresis result of linearization enzyme digestion products of the plasmid expression vector,
where lane 1: DL10000 DNA Marker (10,000 bp, 7,000 bp, 4,000 bp, 2,000 bp, 1,000 bp, 500 bp, and 250 bp),
lane 2: the plasmid pXC4-VZV gE-Fc, and
lane 3: the linearized plasmid VZV gE-Fc-straight.
Figure 4:
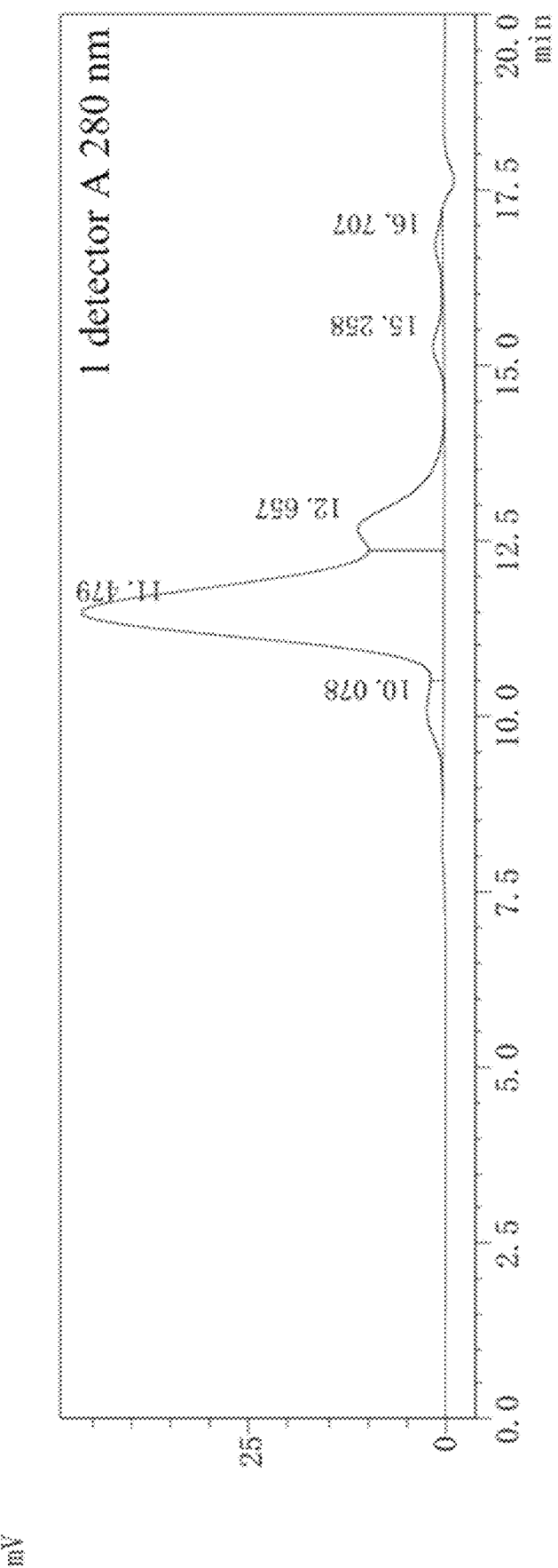
FIG. 4 shows an HPLC-SEC chromatogram of a recombinant VZV gE protein purified by affinity chromatography.

The TaKaRa MiniBest Agarose Gel Extraction Kit was used to recover the target fragment (shown by an arrow in FIG. 1). With sticky-end ligation technology, recovered digestion products gE-Fc-H/E and pXC-H/E were subjected to ligation at 16° C. for 6 h through TaKaRa DNA Ligation Kit LONG (TaKaRa), and then a ligation product was transformed into competent DH5α and subjected to inverted cultivation at 37° C. for 15 h; two clones gE-Fc-1 and gE-Fc-2 were screened out by colony PCR screening (FIG. 2); with pXC-F and pXC-R as primers and the plasmid gE-Fc-1 as a template, the target gene was amplified by PCR, with a size of about 2,400 bp; an amplification product was sequenced by Beijing Huada Gene, and the whole sequence was determined by adding two additional reactions; and a sequencing result was analyzed by the software BioEdit7.0.9.0, and it was found that the sequence of the colon gE-Fc-1 was exactly the same as the designed sequence. Sequencing primers:

```
pXC-F:
5'-TAACAGACTGTTCCTTTCCATG-3' pXC-R:
5'GTAAAACCTCTACAAATGTGGT-3'

1-F:
5'-AGCACATCTGCCTGAAGC-3'

1-F1:
5'-GCTTATTGTCTGGGCATCT-3'
```

Figure 5:
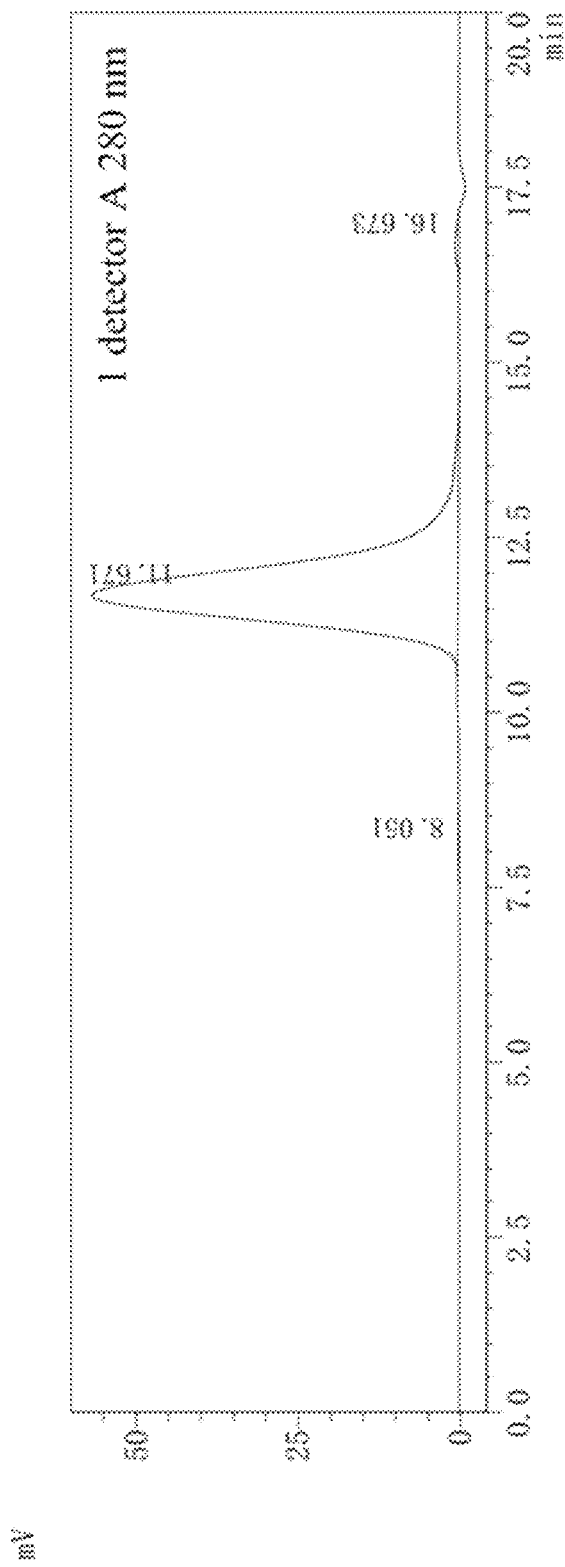
FIG. 5 shows an HPLC-SEC chromatogram of a recombinant VZV gE protein.

The clone gE-Fc-1 was inoculated into 300 ml of an LB (Amp⁺) medium and cultivated at 37° C. and 180 rpm for 16 h; the plasmid pXC-VZV gE-Fc was extracted using a large-quantity/large plasmid extraction kit (Beijing Biomed Gene Technology Co., Ltd.); and the plasmid was linearized by endonuclease PvuI (TaKaRa), purified by extraction with phenol/chloroform/isoamyl alcohol, precipitated with ethanol, and re-dissolved in 1 ml of sterile TE Buffer (TaKaRa). The gel electrophoresis result of the plasmid pXC-VZV gE-Fc and the linearized plasmid VZV gE-Fc-straight was shown in FIG. 3.

Example 2. Establishing and Screening of Stable Cloned Strains

In a sterile laminar flow bench, a perforation voltage of a gene pulse generator Xcell (Bio-Rad) was set as follows: 300 V, 900 μF single pulse, and infinite resistance; a disposable electroporation cuvette (Bio-Rad) with a gap of 4 mm was taken out and added with 40 μg of a linearized plasmid DNA (100 μl) and 0.7 ml of a CHO K1 cell suspension ($1.5\times10^7$ cells/ml), and the linearized plasmid VZV gE-Fc-straight was directly transfected into CHO K1 cells by electrotransfection; the cells in the electroporation cuvette were transferred into a triangular culture flask, 30 ml of a CD CHO medium (GIBCO) was added, and the cells were cultivated in a shaker at 36° C. to 37° C., 5% $CO_2$, and 135 rpm for 24 h; then the cells were collected by low-speed centrifugation and inoculated into a 50 μM MSX-containing CD CHO medium (without glutamine) instead; a resulting cell suspension was transferred into a 96-well flat-bottom culture plate by limiting dilution, and the culture plate was incubated in a 37° C. and 10% $CO_2$ incubator; the cells were observed under an inverted microscope, and monoclonal cell wells were marked; then the monoclonal lines with high expression were screened out by ELISA (goat anti-human IgG+expression product VZV gE-Fc+goat anti-human IgG-HRP) and protein A HPLC; the screened lines were continuously subcultivated and tested, and finally 3 cell clone lines with high expression of the target gene were obtained, with clone numbers of 5B3, 8D8, and 12C3; and an expression level of the recombinant protein in the culture supernatant was detected according to the feed test and HPLC, and the clone line 5B3 was selected for scale-up experiment.

Example 3. Expression and Purification of a Target Product

The obtained clone line 5B3 was inoculated into a 2 L triangular flask with 500 ml of a CD CHO medium, a cap of the breathable flask was tightened, and then the clone line was cultivated in a rotating shaker at 36° C. to 37° C., 5% $CO_2$, and 135 r/min for 4 d; the 5B3 cells were transferred into a 5 L full-automatic bioreactor with 2.0 L of a CD Opti-CHO medium, and cultivation was conducted under the following parameters: rotational speed: 60 r/min, temperature: 36.5° C., pH: 7.0 to 7.4, and dissolved oxygen (DO): 40% to 60%; a sample was collected every day to detect cell viability, cell density, and glucose content; 4 d after the cultivation (when a viable cell density increased to $5\times10^6$ to $7\times10^6$ cells/ml), 200 ml to 300 ml of CD Efficient Feed C was supplemented, and then CD Efficient Feed C was supplemented once every other day; the glucose content in the culture was determined every day, where if the glucose content was lower than 11.1 mmole/L, a 40% glucose solution was supplemented to the full-automatic bioreactor through a peristaltic pump until the glucose content reached 22 mmole/L. L; 12 d to 14 d after the cultivation (when a proportion of viable cells decreased to 60% to 70%), the cultivation was stopped; and a culture was centrifuged at 12,000 r/min (or using a 3 M depth filter) to remove cells and cell debris and collect a cell culture supernatant. The culture supernatant was filtered through a 0.45 μm filter membrane, and a filtrate was allowed to pass through a Protein A gel chromatography column (Mabselect™ Sure, MabSelect™ Sure LX, MabCapture™ A, AT Besterose A, etc.) pre-equilibrated with 40 mM PBS (pH 7.4, 150 mM NaCl); the column was rinsed with 2 to 4 column volumes of 40 mM PBS until $A_{280}$ returned to a baseline level, and then a 100 mM glycine-hydrochloric acid buffer (or citric acid-sodium citrate buffer, acetic acid-sodium acetate buffer, PH: 3.0 to 4.0) was used instead to elute a conjugated substance; and a collected eluate was placed at room temperature (18° C. to 25° C.) for 30 min (low pH for virus inactivation), then a pH was adjusted to 7.4 to 8.0 with 0.2 M $Na_2HP0_4$, and a resulting mixture was filtered through a 0.45 μm filter membrane to further remove insoluble particles. A protein solution obtained from purification by Protein A affinity chromatography was assayed by Shimadzu LC-20AT HPLC (BioCore SEC-500, 7.8 mm×30 cm, Suzhou Nanowin Science and Technology Co., Ltd). The main peak (dimer) accounted for about 65% to 78%, the monomer accounted for about 20% to 30%, and there were still some polymer products before the main peak, generally accounting for less than 10%. The chromatogram was shown in FIG. 4.

Then the obtained protein solution with the target product was loaded into DEAE Sepharose 4 Fast Flow (or Q Sepharose 4 Fast Flow, NanoGel 50Q, Besterose DEAE, Besterose Q, POROS Q, POROS XQ, etc.) equilibrated with 20 mM PB (pH: 7.4 to 8.0) buffer; after the loading was completed, the chromatography column was rinsed with 20 mM PB buffer until $A_{280}$ returned to the baseline level; then NaCl solutions at different concentrations were used for gradient elution, and the target protein VZV gE was collected; and the anion exchange chromatography column was rinsed with 1 column volume of a 1.0 M NaCl solution for regeneration and finally equilibrated with 20 mM PB (pH: 7.4 to 8.0) buffer for later use.

The collected VZV gE was purified by Sephacryl S400 HR or another suitable molecular sieve chromatographic column, and a target product was collected, sterilized by filtration, and stored at 2° C. to 8° C.

Purified VZV gE was tested for purity by Shimadzu LC-20AT HPLC under the following conditions: mobile phase: 40 mM PBS (including 0.5 M $Na_2SO_4$, pH 7.5), flow rate: 0.750 ml/min, and analytical column: BioCore SEC500

(7.8×300 mm, Nanowin Science and Technology Co., Ltd; or TSK 5000 SWxl, Toyo Soda), and the $A_{280}$ test results showed that the VZV gE had a purity of more than 98% (as shown in FIG. 5) and a relative molecular weight of about 400 KDa.

Example 4. Formaldehyde Inactivation for the Target Product

The recombinant VZV gE obtained in Example 3 was diluted to 100 μg/ml to 1,000 μg/ml with 20 mM PBS (pH: 7.2 to 8.0, 135 mM NaCl); then a 38% formaldehyde solution was added to a final concentration of 0.1% (v/v) of a total volume of a resulting mixture, and the mixture was placed at 37° C. for 72 h, during which period, the mixture was shaken twice every day for thorough mixing; and then the mixture was placed at 2° C. to 8° C.

Example 5. β-propiolactone Inactivation for the Target Product

The recombinant VZV gE solution obtained in Example 3 was cooled to 2° C. to 8° C. and weighed, then β-propiolactone was added to a final concentration of 0.1% to 0.01% of a weight of the solution, and a resulting mixture was placed at 2° C. to 8° C. for 72 h, during which period, the mixture was shaken twice every day for thorough mixing. 72 h later, the VZV gE solution was heated to 37° C. and kept at the temperature for 4 h such that the β-propiolactone was completely converted into lactic acid, and then the solution was placed at 2° C. to 8° C.

Example 6. Removal of Formaldehyde or β-propiolactone from the Target Product The protein solution with the recombinant VZV gE obtained in Example 5 or 6 was appropriately diluted with 20 mM PB (pH: 7.2 to 8.0) or a 20 mM Tris-HCl solution (pH: 7.2 to 8.0) until a NaCl concentration in the solution was lower than 50 mM; then the VZV gE-containing solution was allowed to pass through a DEAE Sepharose 4FF chromatography column equilibrated with 20 mM PB (or 20 mM Tris-HCl, pH: 7.2 to 8.0); then the column was rinsed with a 20 mM PB solution (or a 20 mM Tris-HCl solution, PH: 7.2 to 8.0) until $A_{280}$ completely returned to the baseline level, and then further rinsed with 4 column volumes of the solution; an eluent with 0.4 M NaCl (a solution with 20 mM PB or 20 mM Tris-HCl, pH: 7.5) was used to elute the VZV gE conjugated on the gel; and a solution with the target product was collected and filtered with a 0.2 μm sterilization filter membrane to obtain a filtrate, which was a vaccine stock solution.

Example 7. Preparation of a Vaccine with an Aluminum Adjuvant

The vaccine stock solution obtained in Example 6 was diluted with 20 mM Tris-HCl (pH: 7.2 to 7.5, including 135 mM to 150 mM NaCl) to 10 μg/ml to 800 μg/ml, a resulting solution was thoroughly mixed with an equal volume of an aluminum hydroxide adjuvant suspension (aluminum content: 0.2 mg/ml to 1.5 mg/ml) at room temperature, and a resulting mixture was placed at 2° C. to 8° C.

The vaccine solution with an aluminum adjuvant was taken out from the 2° C. to 8° C. environment and dispensed into 2 ml vials (or pre-filled glass syringes) under aseptic conditions, with 0.5 ml (or 1.0 ml) per vial, and then the vials were sealed and stored at 2° C. to 8° C. in the dark.

In the table below, the preparation of 1,000 ml vaccines with different VZV gE contents was taken as an example (the first column from the left showed an antigen content in 1 ml of a prepared vaccine, and the first column from the right showed an antigen content in 0.5 ml of a vaccine for routine intramuscular injection). The vaccine stock solution with a VZV gE concentration of 800 μg/ml was used to prepare the vaccines with an aluminum adjuvant, and a preparation method was as follows:

TABLE 1

Preparation of VZV gE vaccine solutions including an aluminum adjuvant with different antigen contents

| VZV gE content (μg/ml) | Stock solution (800 μg/ml) volume (ml) | 20 mM Tris-HCl (ml) | Aluminum adjuvant (ml) | VZV gE content (μg/0.5 ml) |
|---|---|---|---|---|
| 10 | 12.5 | 487.5 | 500 | 5 |
| 20 | 25 | 475 | 500 | 10 |
| 40 | 50 | 450 | 500 | 20 |
| 100 | 125 | 375 | 500 | 50 |
| 200 | 250 | 250 | 500 | 100 |
| 400 | 500 | 0 | 500 | 200 |

Example 8. Lyophilization of the Recombinant VZV gE Fusion Protein

The vaccine stock solution obtained in Example 6 was diluted to 40 μg/ml to 800 μg/ml with 20 mM Tris-HCl (pH: 7.2 to 7.5, including 135 mM NaCl), then a 10% sucrose (or 10% trehalose, 10% mannitol, and 10 lactose) solution was added to a final concentration of 3%, and a VZV gE concentration in the solution to be dispensed was adjusted to 20 μg/ml (or 50 μg/ml, 80 μg/ml, 100 μg/ml, 200 μg/ml, and 400 μg/ml); a resulting mixture was thoroughly mixed and then dispersed into 2 ml tube-like bottles, with 1.0 ml per bottle, and the bottles were partially stoppered with butyl rubber stoppers and then placed in a lyophilization bin; with a pre-freezing temperature set to −40° C. to −45° C., the vaccine solution was frozen for 4 h, and then vacuum pumping was conducted for lyophilizing, where an automatic temperature rise program was adopted for temperature control: increasing for 6 h from −40° C. to −25° C., increasing for 4 h from −25° C. to −5° C., holding at 0° C. to 5° C. for 1 h, holding at 25° C. for 1 h, and holding at 35° C. for 6 h to 8 h; and then the butyl rubber stoppers were tightly pressed down under vacuum (or introduced with high-purity nitrogen or argon for pressing).

The stoppered bottles were taken out from the lyophilization bin and sent to an automatic capping machine to tighten the aluminum caps. Then the bottles were stored in a cold storage at 2° C. to 8° C.

Before use, 1.0 ml of water for injection or an aluminum hydroxide adjuvant suspension was drawn with a disposable sterile syringe and injected into a bottle with lyophilized VZV gE, and a resulting mixture was mixed gently for about 5 min to obtain a vaccine without visible particles. The vaccine should be used immediately after dissolution, or should be used within 30 minutes after dissolution at latest. This vaccine should be used for subcutaneous or intramuscular injection and is prohibited from being used for intravenous injection.

Example 9. Animal Immunization Experiment

The vaccine that included 100 μg/ml of VZV gE and an aluminum adjuvant for adsorption was taken out from the cold storage at 2° C. to 8° C. and diluted with 20 mM Tris-HCl to obtain solutions with 8 µg/ml and 2 µg/ml of VZV gE, and then an equal volume of an aluminum adjuvant was added to obtain aluminum adjuvant-containing vaccines with 4 µg/ml and 1 µg/ml of VZV gE (or 2 µg/ml and 0.5 µg/0.5 ml of VZV gE) for the animal experiment.

4 to 6 week-old female BALB/C mice were randomly divided into 5 groups, 8 in each group. Each mouse in the control group was intraperitoneally injected with 0.5 ml of an aluminum adjuvant. Mice in the 4 experimental groups were intraperitoneally injected with 0.5 ml of the aluminum adjuvant-containing vaccine at VZV gE dosages of 50 µg, 10 µg, 2 µg, and 0.5 µg. 8 mice were used for each dosage group. After the initial immunization, immunization was conducted once every two weeks, with a total of 4 immunizations. Blood was collected from the tail vein 7 d after the second and third immunizations, and serum was isolated and cryopreserved at −70° C. Blood was collected from the heart 7 d after the fourth immunization, and serum was isolated and cryopreserved at −70° C.

Figure 6:
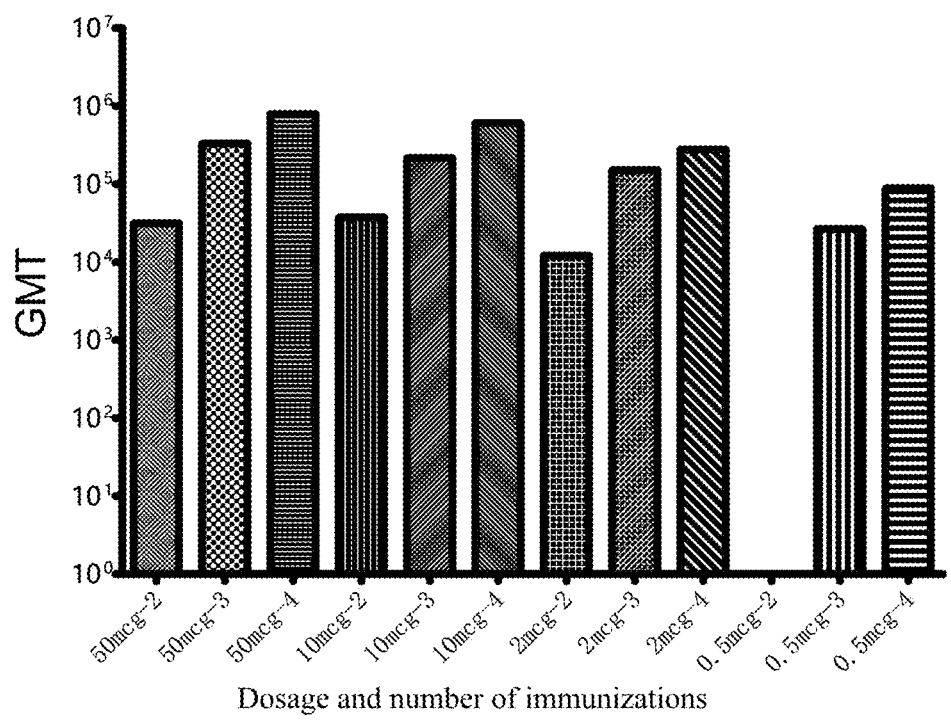
FIG. 6 shows the titer (geometric mean titer (GMT)) of serum antibodies produced in mice immunized with a VZV gE vaccine including an aluminum adjuvant at various dosages.

Antibody titer determination by ELISA: The recombinant VZV gE-His protein was diluted to 1 µg/ml with a carbonate buffer, coated on a 96-well microplate (Costar) at 100 µl/well, placed at 37° C. for 1 h, and then placed overnight at 2° C. to 8° C.; the liquid in the 96-well plate was discarded, and then the plate was washed 3 times with 20 mM PBS; 200 µl of a blocking solution (2% bovine serum albumin (BSA) and component V) was added to each well, and blocking was conducted at room temperature for 60 min; the solution in the wells was removed, and the plate was washed 3 times with a 20 mM PBS-T solution; mouse serum pre-diluted at 1:50 (or 1:500 or 1:1,000) was added to wells in the first column on the 96-well microplate, and then 2-fold serial dilution was conducted, where only mouse serum (1:100) immunized intraperitoneally with an aluminum adjuvant was used for the negative control; reaction was conducted at 37° C. for 60 min, then the solution in the wells was removed, and the plate was washed 3 times with a 20 mM PBS-T solution; the goat anti-mouse IgG-HRP conjugate was taken and diluted with an enzyme conjugate diluent at 1:100 (the diluent included 1 mg/ml of human IgG), pre-reacted for 30 min at room temperature, and then added to the 96-well microplate at 100 µl/well; reaction was conducted at 37° C. for 30 min, the blocking solution in the wells was removed, and then the plate was washed 3 times with a 20 mM PBS-T solution; 100 µl of a TMB chromogenic solution was added to each well, and 10 min later, 50 µl of a stop solution was added to stop the reaction; then the TECAN Infinit 200 microplate reader was used to determine $A_{450}$ absorbance values; and a value 3 times a $A_{450}$ value of the mixed serum in the negative control was taken as a Cut-Off value (if the $A_{450}$ value in the negative control was lower than 0.100, it was counted as 0.100) to determine the titer of immunized serum. The geometric mean and standard deviation of the anti-VZV gE antibody titers in serum of mice in each experimental group were shown in Table 2 below. After the second immunization, except that 1 mouse in the lowest-dosage group (0.5 µg) was not positive for the serum antibody, all mice were positive for the serum antibody. The statistical analysis of the antibody titers determined for experimental mice in each group showed that, after the third immunization, the serum antibody titer of experimental mice in each dosage group was significantly higher than that after the second immunization; after the fourth immunization, the serum antibody titer was partially increased, which was insignificant; and after the second, third, and fourth immunizations, there was no significant difference in the serum antibody titer among mice in the three high-dosage groups. The serum antibody titers of BALB/C mice immunized with VZV gE vaccines with an aluminum adjuvant at various dosages were shown in FIG. 6.

Serum neutralizing antibody titer determination: VZV is a virus that can cause cell fusion lesions on human embryonic lung diploid cells. Therefore, the virus plaque reduction neutralization test can be used to test the ability of antibodies with different serum dilutions to neutralize the virus, and a serum titer at which the number of plaques is reduced by 50% is calculated. The virus neutralization test with serum antibodies is the most direct test to detect whether there are antibodies that can neutralize VZV in immunized serum. This test has disadvantages such as cumbersome operations, low sensitivity, high manpower cost, large time consumption, and inability to use equipment for automatic interpretation, and the calculation of $ED_{50}$ requires professional data processing software. Due to the above problems, few people use this test to determine serum neutralizing antibodies. Due to the large consumption of serum in this test, the neutralizing antibody determination was conducted only on mouse serum collected after the last immunization.

This test was a VZV serum neutralization test conducted on a flat-bottomed 96-well microplate, and MRC-5 cells sensitive to VZV (purchased from ATCC) were used as a cell matrix. The serum frozen in a refrigerator at −70° C. was taken out and thawed at room temperature, diluted at 1:10 with a 10% FBS-containing 199 medium (GIBCO) in a sterile clean bench, and then 4-fold diluted serially in a 96-well plate, with a total of 7 dilutions and two wells for each dilution. The rabbit anti-VZV gE serum was adopted as the positive control serum, and mixed serum of mice immunized with an aluminum adjuvant (diluted at 1:10) was adopted as the negative control serum. On each 96-well plate, 6 virus solution control wells and 6 cell control wells were set. The diluted serum to be tested was mixed with a specified amount of OKA virus (purchased from ATCC in the United States), and then the 96-well microplate was covered. The microplate was shaken on a shaker for 30 s and then placed in a 10% $CO_2$ and 37° C. incubator (10%), and reaction was conducted for 30 min.

A culture flask with a single layer of confluent MRC-5 cells (ATCC, generation 25 to 38) was taken out from the $CO_2$ incubator, the medium in the T75 culture flask (Corning) was removed in a hundred-level clean bench, and 5 ml of a 0.25% trypsin (GIBCO) solution was added to digest the single layer of MRC-5 cells; a resulting mixture reacted for 3 min at room temperature, then the trypsin solution was removed, and 10 ml of a cell culture medium was added; and an inner surface of the cell culture flask was gently rinsed to disperse the MRC-5 cells, and a specified volume of cell culture medium was added to obtain a cell suspension. The 96-well microplate with the serum to be tested was taken out from the incubator, the cell suspension was added with a multi-channel pipette, and the plate was covered; the microplate was shaken on a shaker for 30 s, and then incubated in a 37° C. $CO_2$ incubator (10%) for 3 d to 4 d; and 48 h later, the cytopathic effect in each well was observed with an inverted microscope every day, and the number of plaques in each well was accurately counted and recorded. 96 h later, a 12-channel pipette was used to transfer the liquid in each well into a waste liquid tank with 0.1% sodium hypochlorite, 0.1% crystal violet was added to stain for 1 h, and after destaining, the microplate was placed on absorbent paper in an inverted manner and dried at room temperature.

Figure 7:
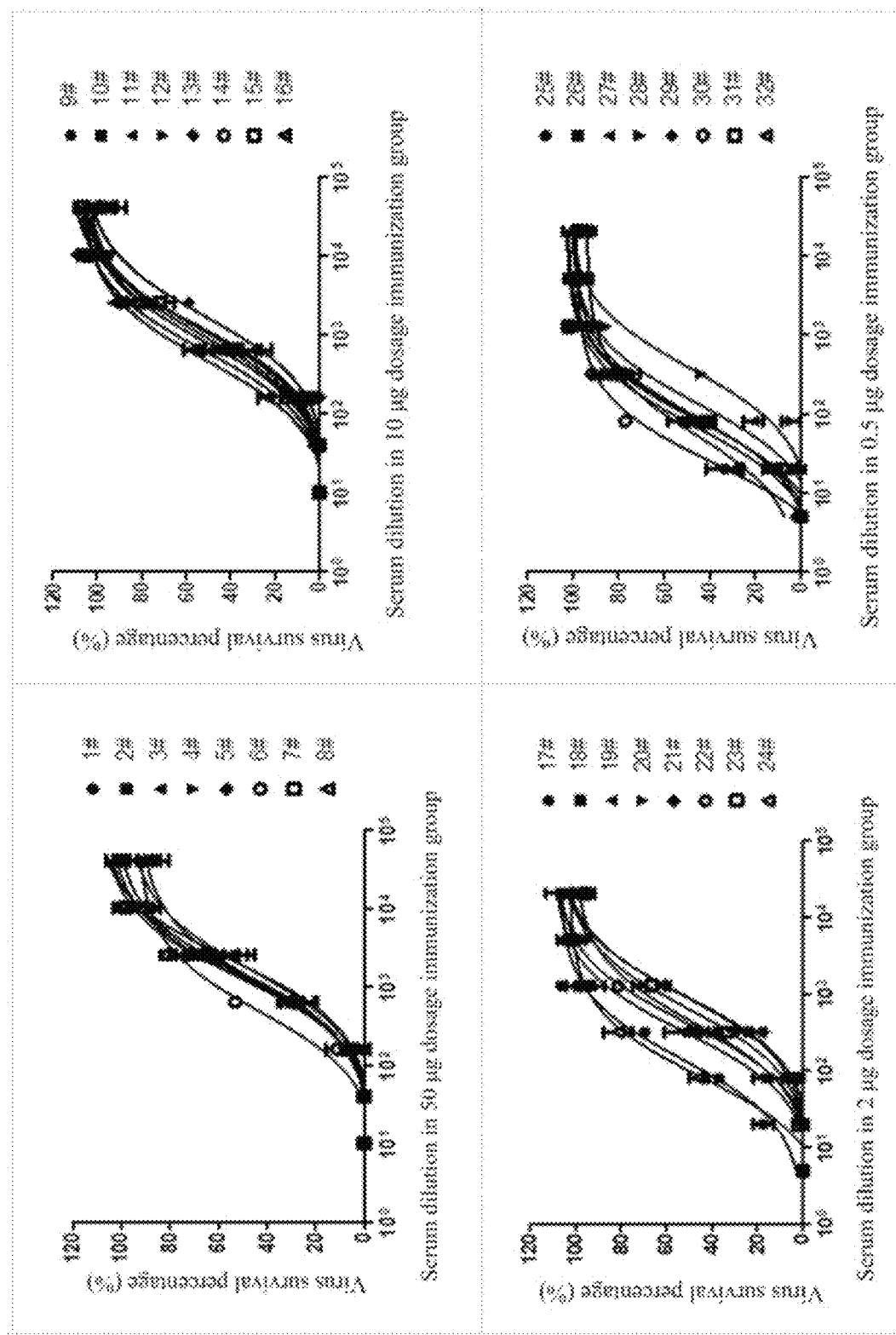
FIG. 7 shows the titer determination results of serum neutralizing antibodies produced in BALB/C mice immunized with a recombinant VZV gE vaccine including an aluminum adjuvant for adsorption.
Figure 8:
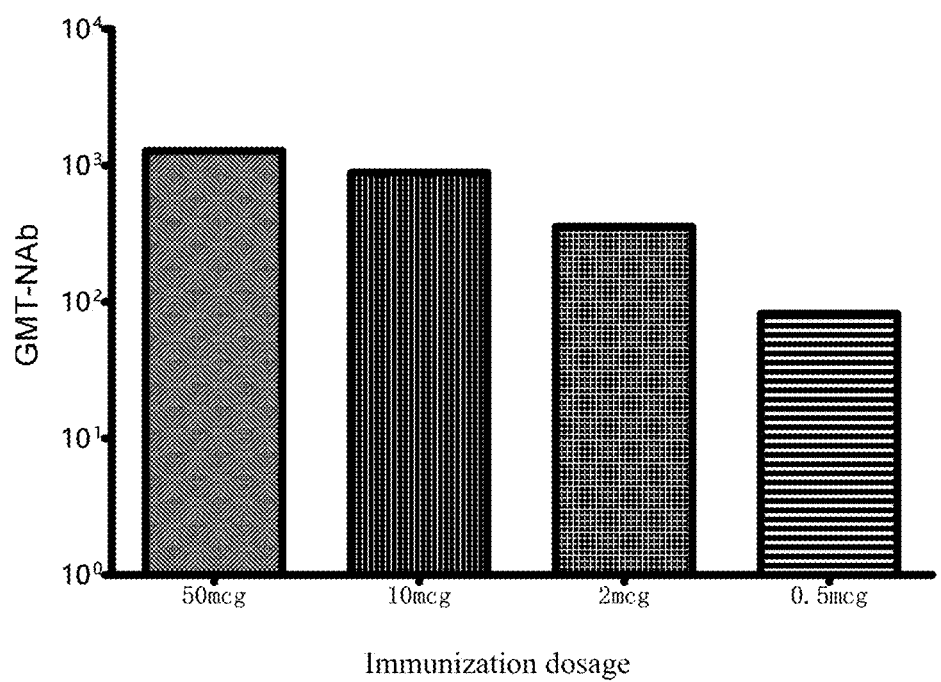
FIG. 8 shows the GMT of neutralizing antibodies produced in BALB/C mice immunized with a VZV gE vaccine including an aluminum adjuvant at different dosages.

The number of plaques in each serum sample at each dilution was entered into an EXCEL 2016 table. With an average number of plaques in the virus solution wells (average of 6 wells, 25 to 30 per well) as 100%, the reduced number of plaques in serum at each dilution was calculated and converted into a percentage, and then the $ED_{50}$ value was calculated from the data with Prism 5.0 software. The $ED_{50}$ value is the serum titer at which the number of plaques is reduced by 50%. The serum neutralizing antibody titer $ED_{50}$ determination curve for each mouse in the four dosage groups was shown in FIG. 7, and the GMT of serum neutralizing antibodies and the distribution of neutralizing antibody titers in each dosage group were shown in Table 3. The comparison of GMT of VZV serum neutralizing antibodies among the dosage groups was shown in FIG. 8, and it can be seen from the figure that the neutralizing antibody titer of the lowest dosage group was significantly lower than that of the other three groups, and the serum neutralizing antibody titers of the other three groups all reached a high level.

TABLE 2

Serum antibody titers of BALB/C mice immunized with a VZV gE vaccine including an aluminum adjuvant at different dosages (ELISA)

| Administration group | Number of immunizations | Minimum | Lower quartile | Median | Upper quartile | Maximum | GMT | SD |
|---|---|---|---|---|---|---|---|---|
| 50 μg | 2 | 15996 | 15996 | 31989 | 63973 | 63973 | 31989 | 1.90 |
| | 3 | 255859 | 255859 | 255859 | 511682 | 511682 | 331894 | 1.43 |
| | 4 | 511682 | 511682 | 1023293 | 1023293 | 1023293 | 788860 | 1.43 |
| 10 μg | 2 | 15996 | 31989 | 31989 | 53827 | 127938 | 38019 | 1.85 |
| | 3 | 127938 | 152055 | 255859 | 255859 | 255859 | 215278 | 1.38 |
| | 4 | 255859 | 511682 | 511682 | 1023293 | 1023293 | 609537 | 1.63 |
| 2 μg | 2 | 500 | 9506 | 22646 | 31989 | 31989 | 13459 | 4.15 |
| | 3 | 63973 | 127938 | 127938 | 255859 | 255859 | 152055 | 1.63 |
| | 4 | 127938 | 152055 | 255859 | 511682 | 511682 | 279254 | 1.78 |
| 0.5 μg | 2 | 1 | 100 | 2000 | 2000 | 3999 | 474 | 16.98 |
| | 3 | 2000 | 9506 | 45290 | 63973 | 255859 | 29376 | 4.49 |
| | 4 | 31989 | 38019 | 90573 | 215278 | 255859 | 90573 | 2.29 |

TABLE 3

Serum neutralizing antibody titers of BALB/C mice immunized with a VZV gE vaccine including an aluminum adjuvant for adsorption at different dosages

| | Immunization dosage group | | | |
|---|---|---|---|---|
| Statistics | 50 μ/mouse | 10 μg/mouse | 2 μg/mouse | 0.5 μg/mouse |
| Minimum | 488 | 470 | 84 | 23 |
| Lower quartile | 1213 | 665 | 175 | 59 |
| Median | 1321 | 867 | 428 | 88 |
| Upper quartile | 1660 | 1262 | 859 | 124 |
| Maximum | 2188 | 1698 | 957 | 377 |
| GMT | 1294 | 899 | 378 | 87 |
| SD | 1.55 | 1.51 | 2.38 | 2.20 |

What is claimed is:

1. A recombinant varicella-zoster virus (VZV) vaccine preparation, comprising a fusion protein formed by an amino acid sequence of an extracellular domain of a recombinant glycoprotein gE of a live attenuated VZV strain (OKA strain) gene and an Fc fragment of human immunoglobulin, wherein the fusion protein has an amino acid sequence shown in SEQ ID No. 1.

2. The vaccine preparation according to claim 1, further comprising a vaccine adjuvant.

3. The vaccine preparation according to claim 2, wherein the vaccine adjuvant is an aluminum hydroxide adjuvant, an aluminum phosphate adjuvant, or a mixture of aluminum hydroxide and aluminum phosphate adjuvants.

4. The vaccine preparation according to claim 1, wherein each dosage unit of the vaccine preparation comprises 5 µg to 200 µg of the fusion protein.

5. The vaccine preparation according to claim 4, wherein each dosage unit of the vaccine preparation comprises 10 µg to 100 µg of the fusion protein.

6. The vaccine preparation according to claim 5, wherein each dosage unit of the vaccine preparation comprises 20 µg to 60 µg of the fusion protein.

7. The vaccine preparation according to claim 1, further comprising other substances that can enhance immunogenicity, wherein the other substances that can enhance immunogenicity comprise, but are not limited to: phosphatidylcholine (PC), lecithin, 3D-MPL, long-chain fatty acid (ester), mineral oil, vegetable oil, sodium methylcellulose (MC-Na), sodium carboxymethylcellulose (CMC-Na), and cholesterol-containing liposome.

8. The vaccine preparation according to claim 1, wherein the vaccine preparation is a lyophilized preparation.

9. The vaccine preparation according to claim 8, wherein the lyophilized preparation is dissolved by an aluminum hydroxide adjuvant suspension before use, and then a resulting mixture is thoroughly mixed and injected intramuscularly or subcutaneously.

10. A recombinant gene capable of expressing the fusion protein according to claim 1, wherein the recombinant gene has a DNA sequence shown in SEQ ID No. 2.

* * * * *

SEQUENCE LISTING

<160> NUMBER OF SEQ ID NOS: 6

<210> SEQ ID NO 1
<211> LENGTH: 748
<212> TYPE: PRT
<213> ORGANISM: Artificial Sequence
<220> FEATURE:
<223> OTHER INFORMATION: Fusion protein

<400> SEQUENCE: 1

Ser Val Leu Arg Tyr Asp Asp Phe His Ile Asp Glu Asp Lys Leu Asp
1 5 10 15

Thr Asn Ser Val Tyr Glu Pro Tyr Tyr His Ser Asp His Ala Glu Ser
20 25 30

Ser Trp Val Asn Arg Gly Glu Ser Ser Arg Lys Ala Tyr Asp His Asn

```
            35                  40                  45
Ser Pro Tyr Ile Trp Pro Arg Asn Asp Tyr Asp Gly Phe Leu Glu Asn
 50                  55                  60

Ala His Glu His His Gly Val Tyr Asn Gln Gly Arg Gly Ile Asp Ser
 65                  70                  75                  80

Gly Glu Arg Leu Met Gln Pro Thr Gln Met Ser Ala Gln Glu Asp Leu
                 85                  90                  95

Gly Asp Asp Thr Gly Ile His Val Ile Pro Thr Leu Asn Gly Asp Asp
                100                 105                 110

Arg His Lys Ile Val Asn Val Asp Gln Arg Gln Tyr Gly Asp Val Phe
                115                 120                 125

Lys Gly Asp Leu Asn Pro Lys Pro Gln Gly Gln Arg Leu Ile Glu Val
                130                 135                 140

Ser Val Glu Glu Asn His Pro Phe Thr Leu Arg Ala Pro Ile Gln Arg
145                 150                 155                 160

Ile Tyr Gly Val Arg Tyr Thr Glu Thr Trp Ser Phe Leu Pro Ser Leu
                165                 170                 175

Thr Cys Thr Gly Asp Ala Ala Pro Ala Ile Gln His Ile Cys Leu Lys
                180                 185                 190

His Thr Thr Cys Phe Gln Asp Val Val Asp Val Asp Cys Ala Glu
                195                 200                 205

Asn Thr Lys Glu Asp Gln Leu Ala Glu Ile Ser Tyr Arg Phe Gln Gly
                210                 215                 220

Lys Lys Glu Ala Asp Gln Pro Trp Ile Val Val Asn Thr Ser Thr Leu
225                 230                 235                 240

Phe Asp Glu Leu Glu Leu Asp Pro Pro Glu Ile Glu Pro Gly Val Leu
                245                 250                 255

Lys Val Leu Arg Thr Glu Lys Gln Tyr Leu Gly Val Tyr Ile Trp Asn
                260                 265                 270

Met Arg Gly Ser Asp Gly Thr Ser Thr Tyr Ala Thr Phe Leu Val Thr
                275                 280                 285

Trp Lys Gly Asp Glu Lys Thr Arg Asn Pro Thr Pro Ala Val Thr Pro
290                 295                 300

Gln Pro Arg Gly Ala Glu Phe His Met Trp Asn Tyr His Ser His Val
305                 310                 315                 320

Phe Ser Val Gly Asp Thr Phe Ser Leu Ala Met His Leu Gln Tyr Lys
                325                 330                 335

Ile His Glu Ala Pro Phe Asp Leu Leu Leu Glu Trp Leu Tyr Val Pro
                340                 345                 350

Ile Asp Pro Thr Cys Gln Pro Met Arg Leu Tyr Ser Thr Cys Leu Tyr
                355                 360                 365

His Pro Asn Ala Pro Gln Cys Leu Ser His Met Asn Ser Gly Cys Thr
                370                 375                 380

Phe Thr Ser Pro His Leu Ala Gln Arg Val Ala Ser Thr Val Tyr Gln
385                 390                 395                 400

Asn Cys Glu His Ala Asp Asn Tyr Thr Ala Tyr Cys Leu Gly Ile Ser
                405                 410                 415

His Met Glu Pro Ser Phe Gly Leu Ile Leu His Asp Gly Gly Thr Thr
                420                 425                 430

Leu Lys Phe Val Asp Thr Pro Glu Ser Leu Ser Gly Leu Tyr Val Phe
                435                 440                 445

Val Val Tyr Phe Asn Gly His Val Glu Ala Val Ala Tyr Thr Val Val
450                 455                 460
```

Ser Thr Val Asp His Phe Val Asn Ala Ile Glu Glu Arg Gly Phe Pro
465                 470                 475                 480

Pro Thr Ala Gly Gln Pro Pro Ala Thr Thr Lys Pro Lys Glu Ile Thr
                485                 490                 495

Pro Val Asn Pro Gly Thr Ser Pro Leu Leu Arg Tyr Ala Ala Trp Thr
            500                 505                 510

Gly Gly Leu Ala Glu Pro Lys Ser Cys Asp Lys Thr His Thr Cys Pro
        515                 520                 525

Pro Cys Pro Ala Pro Glu Leu Leu Gly Gly Pro Ser Val Phe Leu Phe
    530                 535                 540

Pro Pro Lys Pro Lys Asp Thr Leu Met Ile Ser Arg Thr Pro Glu Val
545                 550                 555                 560

Thr Cys Val Val Val Asp Val Ser His Glu Asp Pro Glu Val Lys Phe
                565                 570                 575

Asn Trp Tyr Val Asp Gly Val Glu Val His Asn Ala Lys Thr Lys Pro
            580                 585                 590

Arg Glu Glu Gln Tyr Asn Ser Thr Tyr Arg Val Val Ser Val Leu Thr
        595                 600                 605

Val Leu His Gln Asp Trp Leu Asn Gly Lys Glu Tyr Lys Cys Lys Val
    610                 615                 620

Ser Asn Lys Ala Leu Pro Ala Pro Ile Glu Lys Thr Ile Ser Lys Ala
625                 630                 635                 640

Lys Gly Gln Pro Arg Glu Pro Gln Val Tyr Thr Leu Pro Pro Ser Arg
                645                 650                 655

Asp Glu Leu Thr Lys Asn Gln Val Ser Leu Thr Cys Leu Val Lys Gly
            660                 665                 670

Phe Tyr Pro Ser Asp Ile Ala Val Glu Trp Glu Ser Asn Gly Gln Pro
        675                 680                 685

Glu Asn Asn Tyr Lys Thr Thr Pro Pro Val Leu Asp Ser Asp Gly Ser
    690                 695                 700

Phe Phe Leu Tyr Ser Lys Leu Thr Val Asp Lys Ser Arg Trp Gln Gln
705                 710                 715                 720

Gly Asn Val Phe Ser Cys Ser Val Met His Glu Ala Leu His Asn His
                725                 730                 735

Tyr Thr Gln Lys Ser Leu Ser Leu Ser Pro Gly Lys
            740                 745

<210> SEQ ID NO 2
<211> LENGTH: 2244
<212> TYPE: DNA
<213> ORGANISM: Artificial Sequence
<220> FEATURE:
<223> OTHER INFORMATION: DNA expressing the fusion protein

<400> SEQUENCE: 2
agcgtgctgc ggtacgacga tttccacatc gacgaggata agctggacac caatagcgtg      60
tatgagcctt actatcactc cgaccacgcc gagtccagct gggtgaacag gggcgagtct     120
tcccggaagg cttacgacca caactctccc tatatctggc ctagaaatga ctacgatggc     180
tttctggaga cgcccatga gcaccatggc gtgtataatc agggccgggg catcgactct     240
ggcgagagac tgatgcagcc tacacagatg tccgctcagg aggatctggg cgacgataca     300
ggcatccacg tgatcccaac cctgaatggc gacgacagga taagatcgt gaacgtggat     360 cagaggcagt acggcgacgt gttcaagggc gatctgaatc ccaagcctca gggccagcgc     420

```
ctgatcgagg tgtccgtgga ggagaaccat ccattcaccc tgcgcgcccc tatccagcgc    480
atctacggcg tgaggtatac cgagacatgg tcctttctgc ctagcctgac ctgcacaggc    540
gacgctgctc cagctatcca gcacatctgc ctgaagcata ccacatgttt tcaggacgtg    600
gtggtggacg tggattgtgc cgagaataca aaggaggatc agctggctga gatcagctac    660
agattccagg gcaagaagga ggccgatcag ccatggatcg tggtgaacac ctctacactg    720
tttgacgagc tggagctgga ccccccctgag atcgagcctg gcgtgctgaa ggtgctgcgc    780
accgagaagc agtacctggg cgtgtatatc tggaacatga ggggcagcga cggcacctcc    840
acatacgcta ccttcctggt gacatggaag ggcgatgaga agacccggaa tccaacacca    900
gctgtgaccc ctcagccaag aggcgctgag tttcacatgt ggaactatca cagccacgtg    960
ttctccgtgg gcgacacctt tcccctggcc atgcacctgc agtacaagat ccatgaggct   1020
ccattcgacc tgctgctgga gtggctgtat gtgcccatcg atcctacatg ccagcccatg   1080
cgcctgtaca gcacctgtct gtatcaccca aatgcccccc agtgcctgtc ccatatgaac   1140
agcggctgta cctttacatc cccacacctg gcccagaggg tggctagcac agtgtaccag   1200
aactgcgagc atgccgacaa ttacaccgct tattgtctgg gcatctctca catggagcct   1260
tccttcggcc tgatcctgca tgacggcggc accacactga agtttgtgga tacccctgag   1320
agcctgtctg gcctgtacgt gttcgtggtg tacttcaacg ccacgtgga ggccgtggct   1380 tacacagtgg tgtctaccgt ggatcatttc gtgaacgcca tcgaggagag gggatttcca   1440
ccaacagctg gacagcctcc agctaccaca aagcccaagg agatcacacc tgtgaaccca   1500
ggcacctccc ctctgctgag atatgccgct tggaccggcg gcctggctga gcccaaatct   1560
tgtgacaaaa ctcacacatg cccaccgtgc ccagcacctg aactcctggg gggaccgtca   1620
gtcttcctct tccccccaaa acccaaggac accctcatga tctcccggac ccctgaggtc   1680
acatgcgtgg tggtggacgt gagccacgaa gaccctgagg tcaagttcaa ctggtacgtg   1740
gacggcgtgg aggtgcataa tgccaagaca aagccgcggg aggagcagta caacagcacg   1800
taccgtgtgg tcagcgtcct caccgtcctg caccaggact ggctgaatgg caaggagtac   1860
aagtgcaagg tctccaacaa agccctccca gcccccatcg agaaaaccat ctccaaagcc   1920
aaagggcagc cccgagaacc acaggtgtac accctgcctc catctcggga tgagctgacc   1980
aagaaccagg tcagcctgac ctgcctggtc aaaggcttct atcccagcga catcgccgtg   2040
gagtgggaga gcaatgggca gccggagaac aactacaaga ccacgccccc cgtgctggac   2100
tccgacggct ccttcttcct ctatagcaag ctcaccgtgg acaagagcag gtggcagcag   2160
gggaacgtct tctcatgctc cgtgatgcat gaggctctgc acaaccacta cacgcagaag   2220
agcctctccc tgtctccggg taaa                                           2244
```

<210> SEQ ID NO 3
<211> LENGTH: 22
<212> TYPE: DNA
<213> ORGANISM: Artificial Sequence
<220> FEATURE:
<223> OTHER INFORMATION: sequencing primer pXC-F

<400> SEQUENCE: 3

```
taacagactg ttcctttcca tg                                               22
```

<210> SEQ ID NO 4
<211> LENGTH: 22
<212> TYPE: DNA
<213> ORGANISM: Artificial Sequence

```
<220> FEATURE:
<223> OTHER INFORMATION: sequencing primer pXC-R

<400> SEQUENCE: 4
gtaaaacctc tacaaatgtg gt                                            22

<210> SEQ ID NO 5
<211> LENGTH: 18
<212> TYPE: DNA
<213> ORGANISM: Artificial Sequence
<220> FEATURE:
<223> OTHER INFORMATION: sequencing primer 1-F

<400> SEQUENCE: 5
agcacatctg cctgaagc                                                 18

<210> SEQ ID NO 6
<211> LENGTH: 19
<212> TYPE: DNA
<213> ORGANISM: Artificial Sequence
<220> FEATURE:
<223> OTHER INFORMATION: sequenceing primer 1-F1

<400> SEQUENCE: 6
gcttattgtc tgggcatct                                                19
```